(12) United States Patent
Usuda et al.

(10) Patent No.: US 10,349,842 B2
(45) Date of Patent: Jul. 16, 2019

(54) BLOOD PRESSURE MEASURING APPARATUS

(75) Inventors: Takashi Usuda, Tokyo (JP); Yoshiharu Kikuchi, Tokyo (JP); Hideaki Hirahara, Tokyo (JP); Naoki Kobayashi, Tokyo (JP); Katsuyoshi Suzuki, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1413 days.

(21) Appl. No.: 13/211,390

(22) Filed: Aug. 17, 2011

(65) Prior Publication Data

US 2012/0046561 A1 Feb. 23, 2012

(30) Foreign Application Priority Data

Aug. 17, 2010 (JP) ................................. 2010-182150

(51) Int. Cl.
*A61B 5/02* (2006.01)
*A61B 5/0225* (2006.01)
(Continued)

(52) U.S. Cl.
CPC ........ *A61B 5/0225* (2013.01); *A61B 5/02116* (2013.01); *A61B 5/02141* (2013.01); *A61B 5/02225* (2013.01)

(58) Field of Classification Search
CPC ............ A61B 5/02233; A61B 5/02225; A61B 5/6824; A61B 5/02; A61B 5/021; A61B 5/02241; A61B 5/0225
(Continued)

(56) References Cited

U.S. PATENT DOCUMENTS 4,435,835 A 3/1984 Sakow et al.
5,303,711 A * 4/1994 Sciarra .......................... 600/493
(Continued)

FOREIGN PATENT DOCUMENTS

JP 62-284978 A 12/1987
JP 4-40606 U 4/1992
(Continued)

OTHER PUBLICATIONS

Office Action dated Sep. 13, 2013 issued by the Japanese Patent Office in corresponding Japanese Patent Application No. 2010-182150.
(Continued)

*Primary Examiner* — Puya Agahi
(74) *Attorney, Agent, or Firm* — Sughrue Mion, PLLC

(57) ABSTRACT

A blood pressure measuring apparatus, which measures a blood pressure of a living body, includes: a cuff-pressure control unit which controls a cuff pressure of a cuff that presses a part of the living body; an oscillation signal detection unit which detects an oscillation signal from the cuff pressure; a blood pressure specification unit which specifies systolic and diastolic blood pressures as the blood pressure of the living body from the oscillation signal; and a blood pressure determination unit which determines whether systolic and diastolic blood pressures are appropriate or not. The cuff-pressure control unit controls the cuff pressure to be inflated to a first set value, the blood pressure specification unit specifies the systolic and diastolic blood pressures based on a change of an oscillation signal that is detected by the oscillation signal detection unit when the cuff pressure is inflated to the first set value, and when the blood pressure determination unit determines that both the systolic and diastolic blood pressures are appropriate, the
(Continued)

cuff-pressure control unit ends the inflating of the cuff pressure to release the cuff pressure.

11 Claims, 4 Drawing Sheets

(51) Int. Cl.
*A61B 5/021* (2006.01)
*A61B 5/022* (2006.01)

(58) Field of Classification Search
USPC .................................................. 600/489–499
See application file for complete search history.

(56) References Cited

U.S. PATENT DOCUMENTS

| | | | |
|---|---|---|---|
| 5,335,665 A | | 8/1994 | Suzuki |
| 5,518,000 A | | 5/1996 | Booth et al. |
| 5,759,157 A | * | 6/1998 | Harada et al. ................ 600/494 |
| 6,068,601 A | | 5/2000 | Miyazaki et al. |
| 6,171,254 B1 | | 1/2001 | Skelton |
| 2003/0069507 A1 | | 4/2003 | Nishibayashi |
| 2004/0024323 A1 | | 2/2004 | Kulik |
| 2005/0033188 A1 | | 2/2005 | Whitaker et al. |
| 2006/0217617 A1 | * | 9/2006 | Wachtenberg ......... A61B 5/021 600/490 |
| 2009/0018453 A1 | * | 1/2009 | Banet ................. A61B 5/02125 600/493 |

FOREIGN PATENT DOCUMENTS

| | | |
|---|---|---|
| JP | 4-279147 A | 10/1992 |
| JP | 5-31084 A | 2/1993 |
| JP | 7-313473 A | 12/1995 |
| JP | 8-112260 A | 5/1996 |
| JP | 8-322811 A | 12/1996 |
| JP | 2003-11737 A | 4/2003 |
| JP | 2004-65974 A | 3/2004 |
| JP | 2007-259957 A | 10/2007 |

OTHER PUBLICATIONS

Communication dated Dec. 15, 2011 from the European Patent Office in counterpart European application No. 11177781.9.

Communication from the Japanese Patent Office dated Jan. 7, 2014, in a counterpart Japanese application No. 2010-182150.

* cited by examiner

BLOOD PRESSURE MEASURING APPARATUS

BACKGROUND OF THE INVENTION

The present invention relates to a blood pressure measuring apparatus which non-invasively measures the blood pressure.

As a blood pressure measuring apparatus which non-invasively measures the blood pressure, a blood pressure measuring apparatus is usually employed in which the blood pressure is measured by first inflating the cuff pressure to a pressure that is sufficiently higher than the systolic blood pressure (for example, a cuff pressure that is higher than the systolic blood pressure by 40 mmHg), and, while then deflating the cuff pressure, detecting pressure oscillation that is produced in the cuff pressure by pulsation, as an oscillation signal. There is a blood pressure measuring apparatus in which the blood pressure is measured while inflating the cuff pressure, in order to shorten the time required for measurement as compared with the blood pressure measurement that measures the blood pressure while deflating the cuff pressure (for example, see JP-A-8-322811).

In the process of inflating the cuff pressure, however, air is ejected from an air pump to a cuff, and hence periodic oscillation due to driving of the air pump is superimposed as noise on pressure oscillation in the cuff caused by pulsation. In the case where the cycle of the oscillation due to driving of the air pump is similar to that of the pulsation component which is a principal component of a pulse wave, therefore, it is difficult to measure a correct blood pressure from the oscillation signal.

In the related-art blood pressure measurement performed during the process of deflating the cuff pressure, when the systolic blood pressure is to be measured, moreover, the cuff must be pressurized by a pressure which is sufficiently higher than the systolic blood pressure. The pressurization may sometimes cause a burden on the subject (the patient or the like). Therefore, it is requested to develop accurate blood pressure measurement in which the burden on the patient is low, and which can be rapidly performed.

SUMMARY

It is therefore an object of the invention to provide a blood pressure measuring apparatus which can solve the problem that oscillation due to driving of the air pump is superimposed as noise on an oscillation signal and an accurate blood pressure cannot be obtained.

In order to achieve the object, according to the invention, there is provided a blood pressure measuring apparatus, which measures a blood pressure of a living body, the blood pressure measuring apparatus comprising: a cuff-pressure control unit which controls a cuff pressure of a cuff that presses a part of the living body; an oscillation signal detection unit which detects an oscillation signal from the cuff pressure; a blood pressure specification unit specifies systolic and diastolic blood pressures as the blood pressure of the living body from the oscillation signal; and a blood pressure determination unit which determines whether systolic and diastolic blood pressures are appropriate or not, wherein the cuff-pressure control unit controls the cuff pressure to be inflated to a first set value, the blood pressure specification unit which specifies the systolic and diastolic blood pressures based on a change of an oscillation signal that is detected by the oscillation signal detection unit when the cuff pressure is inflated to the first set value, and when the blood pressure determination unit determines that both the systolic and diastolic blood pressures are appropriate, the cuff-pressure control unit ends the inflating of the cuff pressure to release the cuff pressure.

The blood pressure measuring apparatus may further include an air pump which is controlled by the cuff-pressure control unit to eject air to the cuff, thereby inflating the cuff pressure. The cuff-pressure control unit may control the air pump to eject air to the cuff with a cycle which is different from a cycle of a pulse wave.

The cuff-pressure control unit may control the air pump so that the cycle at which the air pump ejects air is a cycle which is shorter than at least one fifth of the cycle of the pulse wave.

A flow of air ejected by the air pump may be from 0.1 L/minute to 3.0 L/minute.

The cuff-pressure control unit may control the cuff pressure to be inflated in a substantially linear manner.

When the blood pressure determination unit determines that at least one of the systolic and diastolic blood pressures is not appropriate, the cuff-pressure control unit may control the cuff pressure to be inflated to a second set value, and then deflated, and the blood pressure specification unit may specify the systolic and diastolic blood pressures based on a change of an oscillation signal that is detected by the oscillation signal detection unit when the cuff pressure is deflated from the second set value.

The cuff-pressure control unit may control the cuff pressure to be deflated in a stepwise manner.

The cuff-pressure control unit may control the cuff pressure to be deflated in a substantially linear manner.

The first set value may be a value which is lower than the second set value, the first set value may be a value which is higher than a systolic blood pressure of the living body, and the second set value may be a value which is higher than a value in which at least 30 mmHg to 50 mmHg is added to a systolic blood pressure of the living body.

The blood pressure measuring apparatus may further include a cuff-size specification unit which specifies a size of the cuff when the cuff pressure is to be inflated. The cuff-pressure control unit may control pressure inflating of the cuff based on the size of the cuff which is specified by the cuff-size specification unit.

The cuff-pressure control unit may inflate or deflate the cuff pressure in a range of 5 mmHg/sec. to 20 mmHg/sec.

DETAILED DESCRIPTION OF EMBODIMENTS

Figure 1:
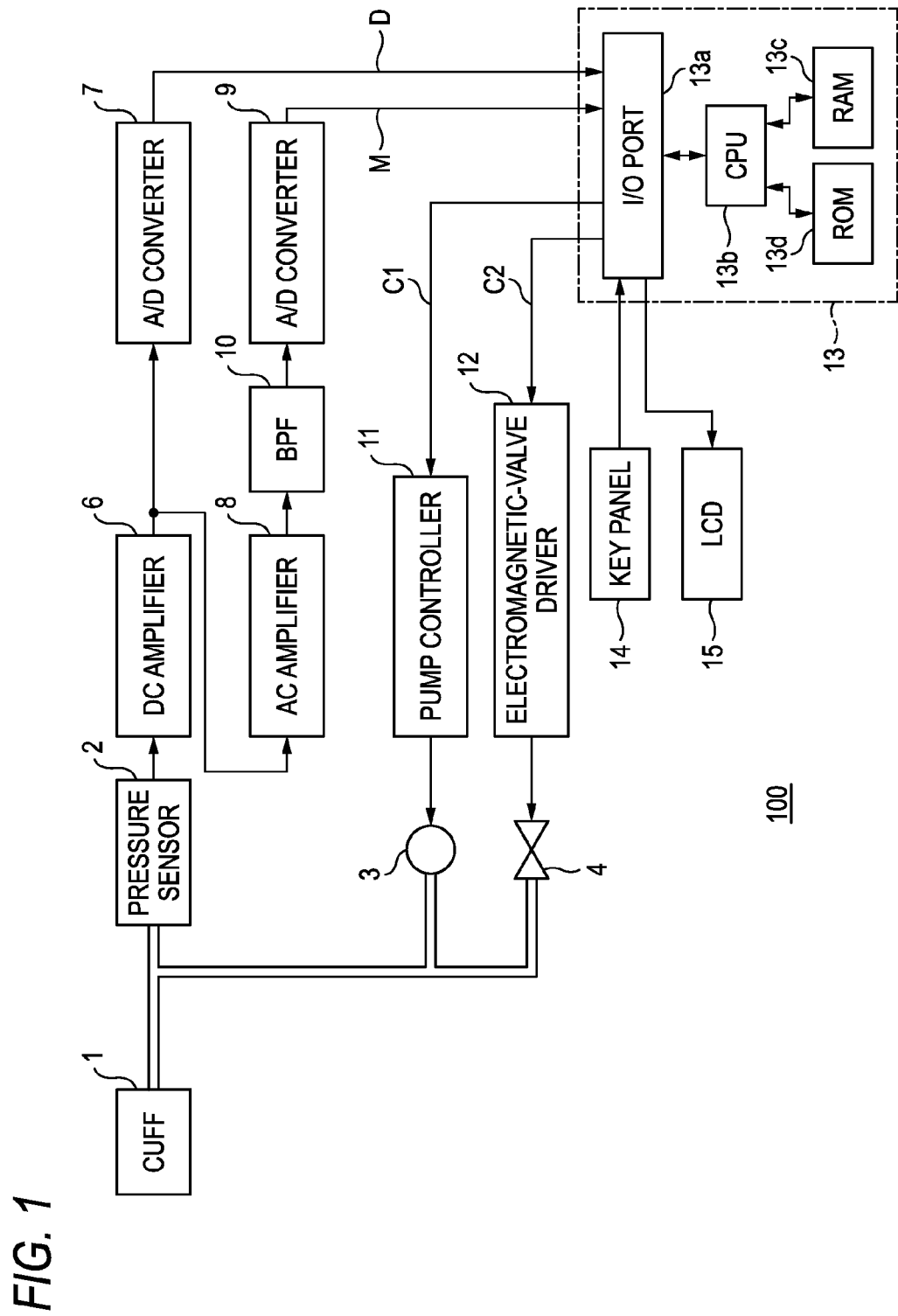
FIG. 1 is a functional block diagram schematically showing a blood pressure measuring apparatus of an embodiment of the invention.

Hereinafter, a blood pressure measuring apparatus 100 of an embodiment of the invention will be described in detail with reference of the drawings. FIG. 1 is a functional block diagram schematically showing the blood pressure measuring apparatus 100. As shown in FIG. 1, the blood pressure measuring apparatus 100 includes a cuff 1, a pressure sensor 2, an air pump 3, an electromagnetic valve 4, a DC amplifier 6, A/D converters 7, 9, an AC amplifier 8, a BPF (Band Pass Filter) 10, a pump controller 11, an electromagnetic-valve driver 12, a controller 13, a key panel 14, and a liquid crystal display (LCD) 15.

In the blood pressure measuring apparatus 100, the pump controller 11, the air pump 3, the electromagnetic-valve driver 12, the electromagnetic valve 4, and the controller 13 function as the cuff-pressure control unit in the invention to control a cuff pressure of a cuff that presses a part of a living body.

The pressure sensor 2, the DC amplifier 6, the A/D converters 7, 9, the AC amplifier 8, the BPF (Band Pass Filter) 10, and the controller 13 function as the oscillation signal detection unit in the invention to detect an oscillation signal from the cuff pressure.

The controller 13 functions also as the blood pressure specification unit and the blood pressure determination unit in the invention, specifies the systolic and diastolic blood pressures as the blood pressure of the living body based on a change of the detected oscillation signal, and determines whether the blood pressure is appropriate or not. The controller 13 functions also as the cuff-size specification unit in the invention, and specifies the size of the cuff when the cuff pressure is to be inflated.

The cuff 1 is wrapped around the finger, the upper arm, a lower leg, or the like of the subject. Air ejected from the air pump 3 in which the principal frequency (usually, 5 Hz or lower) of the oscillation signal is different from that (at least 30 Hz or higher) of ejection noise of air is fed to the cuff 1, and the cuff pressure is inflated. The pump controller 11 controls a driving power to be supplied to the air pump 3, and the cycle of air ejection in accordance with a control signal C1 which is supplied from a CPU (Central Processing Unit) 13b through an I/O port (Input/Output port) 13a.

The air pump 3 is a low-flow air pump such as a rolling pump having a plurality of cylinders (for example, two, three, or four cylinders), and, when the cuff 1 is to be pressurized, is high speed driven. More specifically, the air pump 3 is driven so that the cycle of oscillation due to the operation of ejecting air is very shorter (for example, one fifth or smaller) than that of the principal component of a pulse wave (time waveform of pulsation). In the case where, as described above, the air pump of a low flow (about 0.1 L/minute) is driven (high-speed driven) with a cycle which is very shorter than that of a pulse wave, when a pulse wave is to be measured, the oscillation component of the pressure of air ejected from the air pump 3 can be easily cancelled as described later.

As the air pump 3, an air pump in which the flow of ejected air can be continuously changed from a low flow (about 0.1 L/minute) to a high flow (about 3 L/minute) by changing the driving power and the cycle of air ejection may be used.

The electromagnetic-valve driver 12 receives a control signal C2 from the CPU 13b through the I/O port 13a, and drives the electromagnetic valve 4 in accordance with the contents of the control signal C2, to exhaust the air in the cuff 1.

The pressure sensor 2 detects the air pressure in the cuff 1, i.e., the cuff pressure. An output signal from the pressure sensor 2 undergoes in the DC amplifier 6, a process in which a DC component (a component which does not depend on periodic variations due to a pulse wave or the like) of the signal is amplified, and then is converted to a digital signal in the A/D converter (analog/digital converting circuit) 7. The digital signal which is converted in the A/D converter 7 is sent to the CPU 13b through the I/O port 13a, as a pressure signal D in which the DC component is emphasized.

Also, the output signal of the DC amplifier 6 is subjected to a process in which an AC component (periodic variation component in which a pulse wave component is the principal component) is amplified, and the components other than the pulse wave component is filtered by the BPF 10. As described above, the driving cycle of the air pump 3 is very shorter than the cycle of the principal component of the pulse wave. Therefore, the pulse wave component can be easily separated from the oscillation components of the pressure of the air ejected from the air pump 3.

The A/D converter 9 converts the signal which is filtered by the BPF 10, to a digital signal. The digital signal which is converted in the A/D converter 9 is sent to the CPU 13b through the I/O port 13a, as a pressure signal M containing the principal component of the pulse wave.

The key panel 14 is a controller in which operation keys for performing various operations such as instructions for starting measurement are arranged, and connected to the I/O port 13a. Also the liquid crystal display (LCD) 15 which displays the blood pressure and the like of measurement results on a screen is connected to the I/O port 13a. Displaying means which can display the blood pressure and the like of measurement results on a screen may be, for example, an LED or an organic EL display in place of the liquid crystal display (LCD) 15 in the embodiment.

The controller 13 includes the CPU 13b, the I/O port 13a, a PAM 13c, and a ROM 13d, and controls various parts of the blood pressure measuring apparatus 100. The controller 13 processes various input and detection signals supplied from the parts, and outputs various control signals and a measurement result based on the results of the processes.

The I/O port 13a is an input/output port for the CPU 13b, and connected to the A/D converters 7, 9, the pump controller 11, and the electromagnetic-valve driver 12. The pressure signals D and M which are converted by the A/D converters 7, 9 are supplied to the CPU 13b trough the I/O port 13a, and control signals from the CPU 13b are sent to the pump controller 11 and the electromagnetic-valve driver 12 through the I/O port 13a.

The RAM (Random Access Memory) 13c which is data holding means connected to the CPU 13b sequentially stores data of processing processes. The ROM (Read-Only memory) 13d which is connected to the CPU 13b stores process programs of the CPU 13b.

The CPU 13b calculates the value of the oscillation signal based on the input pressure signals D and M. Then, the CPU 13b performs sampling at each predetermined timing of the calculated waveform of the oscillation signal, and calculates the amplitude. When the cuff pressure is inflated, the calculated amplitude is gradually increased. After the timing when the amplitude becomes maximum, the calculated amplitude is gradually decreased.

Based on a change of the oscillation amplitude due to a temporal change of the cuff pressure, the CPU 13b specifies the systolic and diastolic blood pressures as blood pressures of the subject. Then, the CPU 13b determines whether the blood pressures are appropriate or not. More specifically, the CPU 13b determines whether the specified blood pressures are an inappropriate blood pressure due to body motion or arrhythmia of the subject or not, based on previously stored criteria. If both the specified systolic and diastolic blood pressures are determined as a appropriate value, the CPU 13b sends the control signal C1 indicating that the driving of the air pump 3 is stopped, to the pump controller 11 in order that the cuff pressure is inflated to a first set value and then the pressure rising is ended. Furthermore, the CPU 13b sends the control signal C2 indicating that the electromagnetic valve 4 is fully opened and air in the cuff 1 is exhausted, to the electromagnetic-valve driver 12 in order that, when the rising of the cuff pressure is ended, the cuff pressure is immediately released. The first set value is higher than the systolic blood pressure, and lower than a set value (preferably, a value which is higher than the systolic blood pressure by about 30 to 50 mmHg, hereinafter referred to as the second set value) which is used in usual pressure-deflating measurement.

The first set value may be a fixed value, or a value which can be adequately changed based on a change of the oscillation amplitude that is obtained during pressure-inflating measurement.

By contrast, if at least one of the systolic and diastolic blood pressures is not determined as a appropriate value, the CPU 13b sends the control signal C1 indicative of the driving of the air pump 3 until the cuff pressure reaches a preset pressurization target (second set value), to the pump controller 11. When the cuff pressure reaches the pressurization target, the CPU 13b sends the control signal C2 indicating that the electromagnetic valve 4 is intermittently opened and the cuff pressure is deflated in a stepwise manner, to the electromagnetic-valve driver 12. Then, the CPU 13b calculates the value of the oscillation signal when the cuff pressure is deflated, in the same manner as described above, and, based on a change of the value, specifies the systolic and diastolic blood pressures of the subject. Although the blood pressure measurement performed while deflating the cuff pressure in a stepwise manner requires a prolonged time cycle as compared with that performed while deflating the cuff pressure in a linear manner, the blood pressure measurement can surely measure the oscillation signal, and hence can be accurately performed.

Figure 2:
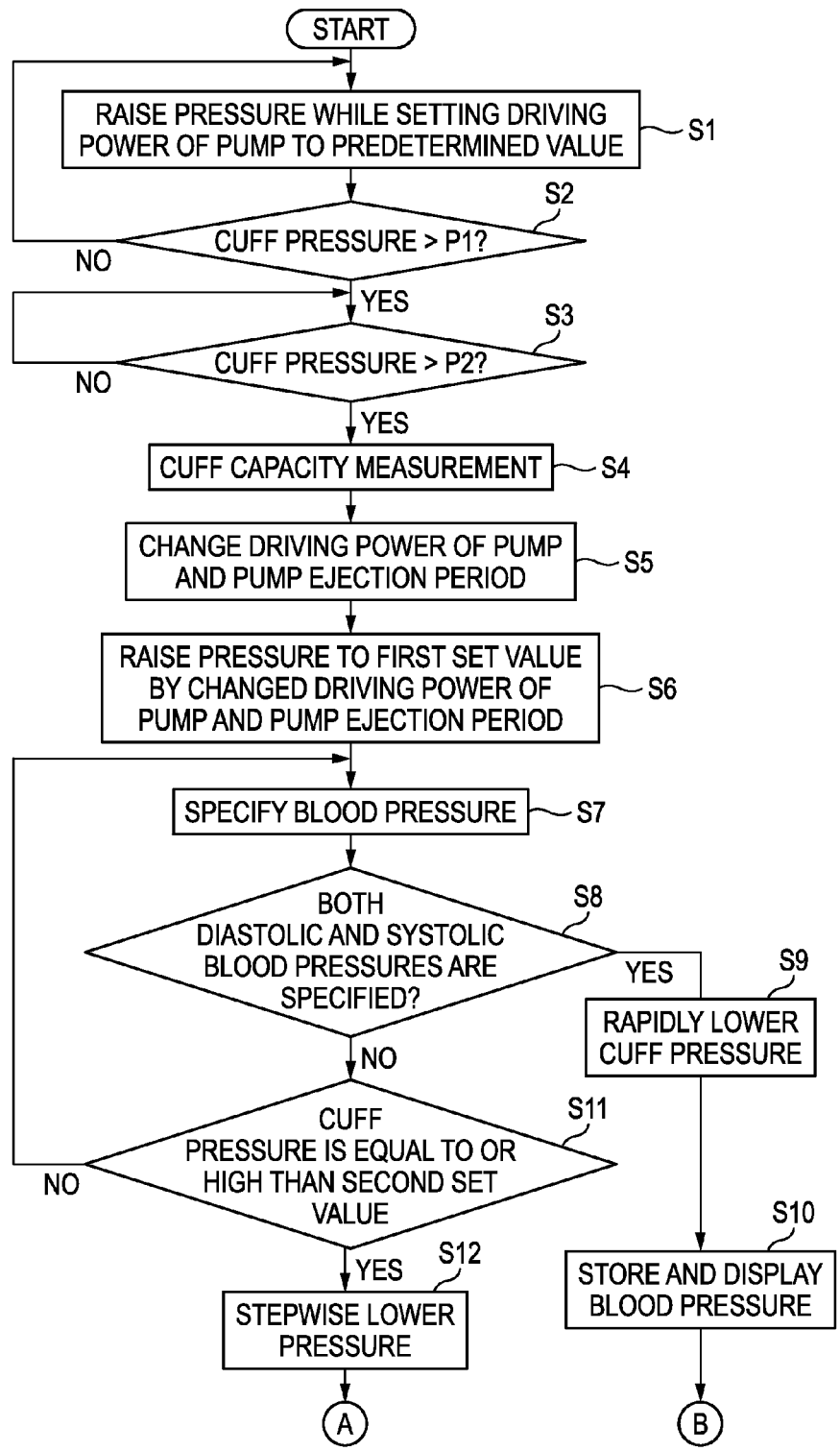
FIG. 2 is a flowchart (No. 1) illustrating the operation of the blood pressure measuring apparatus.
Figure 3:
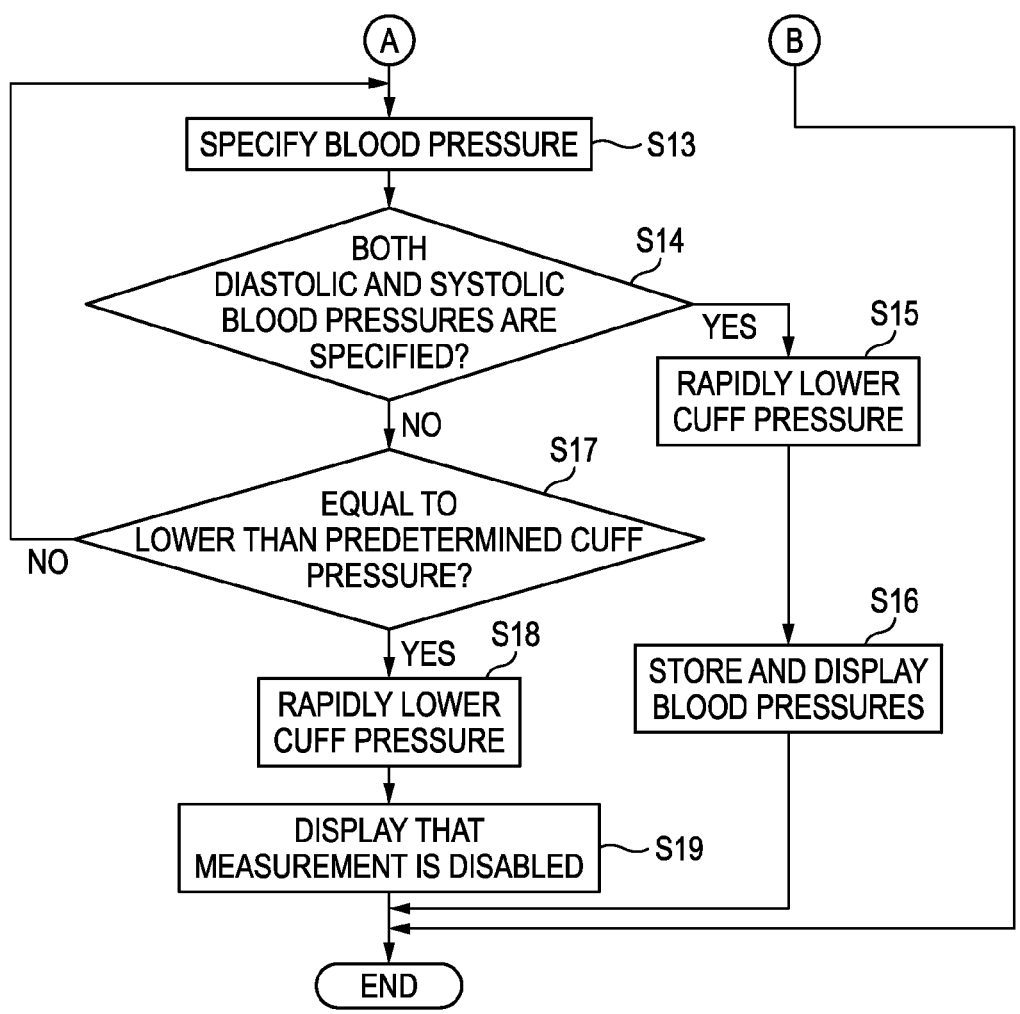
FIG. 3 is a flowchart (No. 2) illustrating the operation of the blood pressure measuring apparatus.

Next, the operation of the blood pressure measuring apparatus of the embodiment of the invention will be described with reference to FIGS. 2 and 3. FIG. 2 is a flowchart (No. 1) illustrating the operation of the blood pressure measuring apparatus 100, and FIG. 3 is a flowchart (No. 2) illustrating the operation of the blood pressure measuring apparatus 100.

First, the cuff 1 is wrapped around a finger or upper arm portion of the subject, and then a button for starting the measurement in the key panel 14 is pressed. The CPU 13b sends the control signal C1 to the pump controller 11 while setting the driving power of the air pump 3 to a predetermined value (for example, the duty of driving power of the air pump is set to 100%). The pump controller 11 drives the air pump 3 with constant driving power to inflate the cuff pressure (step S1). The duty of driving power of the air pump is a ratio of the pulse interval and the pulse width in the case where the air pump 3 is driven by giving a voltage pulse of a constant interval to the air pump.

In next step S2, the CPU 13b determines whether the cuff pressure due to the pressure signal D is higher than a first cuff pressure P1 (for example, 15 mmHg) that is lower than the minimum pressure or not. The air pump 3 is controlled through the pump controller 11 so as to inflate the cuff pressure until the determination in step S2 is YES.

If the determination in step S2 is YES, the CPU 13b starts the time count, and determines whether the cuff pressure is higher than a second cuff pressure P2 (for example, 20 mmHg) that is lower than the minimum pressure or not (step S3).

The first cuff pressure P1 is requested to be a value in the range between 15 mmHg and 45 mmHg, the second cuff pressure P2 is requested to be a value in the range between 20 mmHg and 50 mmHg, and the pressures are requested to satisfy the relationship of P1<P2.

If the determination in step S3 is YES, the CPU 13b terminates the time counting, calculates the cuff capacity value from the counted time cycle (the time required for inflating from P1 to P2) and the air election amount of the air pump 3 per unit time, and stores the obtained cuff capacity value in the RAM 13c (step S4: cuff capacity measurement).

Namely, when the cuff capacity value is measured in the above-described procedure, the controller 13 functions as a cuff-size specification unit which specifies the size of the cuff when the cuff pressure is inflated.

Next, the CPU 13b calculates the duty of driving power of the air pump and the pump ejection cycle (the cycle at which air is ejected) in the subsequent inflating of the pressure in accordance with the cuff capacity value (stored in the RAM 13c) which is obtained in the cuff capacity measurement in step S4, and changes the control signal C1 so as to drive the air pump 3 at the duty of driving power of the air pump and pump ejection cycle which are calculated (step S5).

In accordance with the change, the pump controller 11 drives the air pump 3 in accordance with the duty of driving power of the air pump and pump election cycle which are changed, to inflate the cuff pressure to the first set value (step S6).

Namely, the cuff-pressure control unit controls the inflating of the pressure of the cuff based on the cuff capacity value (the specified cuff size) which is measured in the above procedure.

As described above, based on the cuff capacity value, i.e., the size of the capacity of the cuff 1, the driving ability (more specifically, the inclination of the line in the case where the cuff pressure is inflated in a linear manner) of the air pump 3 when the cuff pressure is inflated can be changed, and hence it is possible to cope with cuffs of different sizes.

Figure 4:
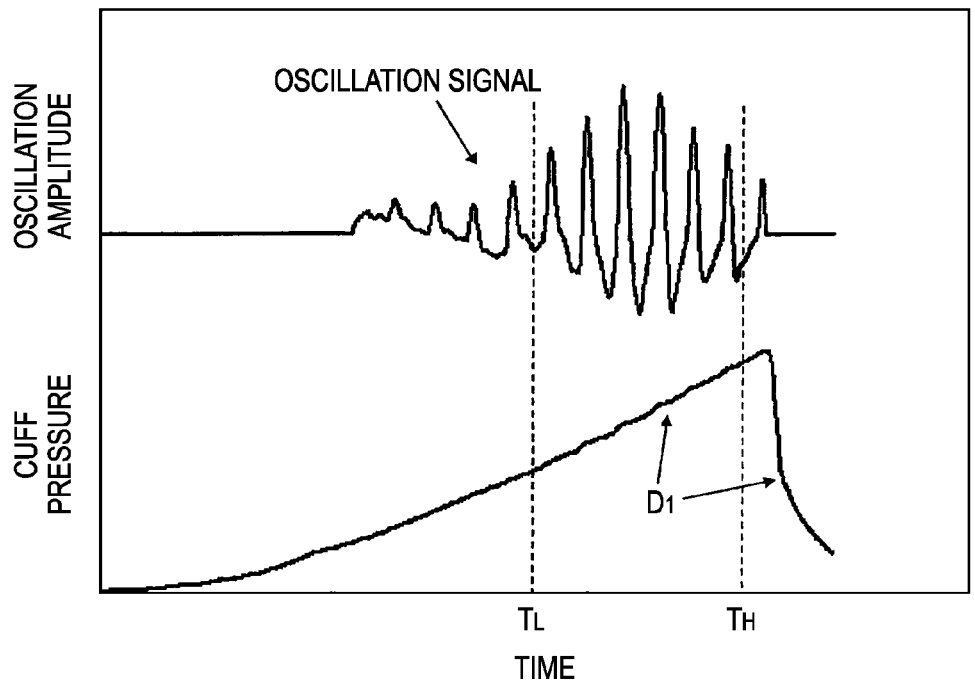
FIG. 4 is a view showing an oscillation signal and the waveform of a cuff pressure in blood pressure measurement during a process of inflating the cuff pressure in the blood pressure measuring apparatus.

In step S6 above, the cuff pressure is inflated by driving the air pump 3, and the cuff pressure $D_1$ due to the pressure signal D which is detected by the pressure sensor 2 is inflated as shown in FIG. 4. FIG. 4 is a view showing the oscillation signal and the waveform of the cuff pressure in blood pressure measurement during a process of inflating the cuff pressure in the blood pressure measuring apparatus 100. At this time, as the pressure inflating rate, a constant rate in the range of, for example, 5 mmHg/sec. to 20 mmHg/sec. is set as a target. As shown in FIG. 4, when the cuff pressure is inflated, the detected oscillation signal becomes the diastolic blood pressure (minimum blood pressure) at a change point $T_L$ where the amplitude is suddenly increased, the amplitude is gradually reduced after the amplitude is increased and becomes maximum, and the detected oscillation signal becomes the systolic blood pressure (maximum blood pressure) at a change point $T_H$ where the amplitude is suddenly reduced.

When the cuff pressure is inflated, the CPU 13b performs sampling to obtain the amplitude, as described above, finds a change point where the amplitude is suddenly changed, and specifies the diastolic blood pressure (minimum blood pressure) and the systolic blood pressure (maximum blood pressure) (step S7). Then, the CPU 13b determines whether both the diastolic blood pressure (minimum blood pressure) and the systolic blood pressure (maximum blood pressure) can be specified or not (step S8). The systolic blood pressure (maximum blood pressure) may be set to be a value at a timing when the amplitude is smaller than the maximum amplitude of the oscillation signal by a predetermined ratio (for example, an amplitude which is a half of the maximum amplitude).

In the process of specifying the systolic and diastolic blood pressures, any related-art technique may be employed in place of the above-described technique. For example, a cuff pressure at a timing when the amplitude is at 50% of the maximum amplitude of the oscillation signal may be specified as the systolic and diastolic blood pressures.

If the determination in step S8 is YES, the CPU 13b transmits the control signal C2 to the electromagnetic-valve driver 12 to fully open the electromagnetic valve 4, thereby rapidly deflating the cuff pressure $D_1$ which has reached the first set value (step S9). Then, the CPU 13b stores the specified blood pressures in the RAM 13c or displays the blood pressures on the LCD 15, or performs the both operations (step S10), and ends the blood pressure measurement.

Figure 5:
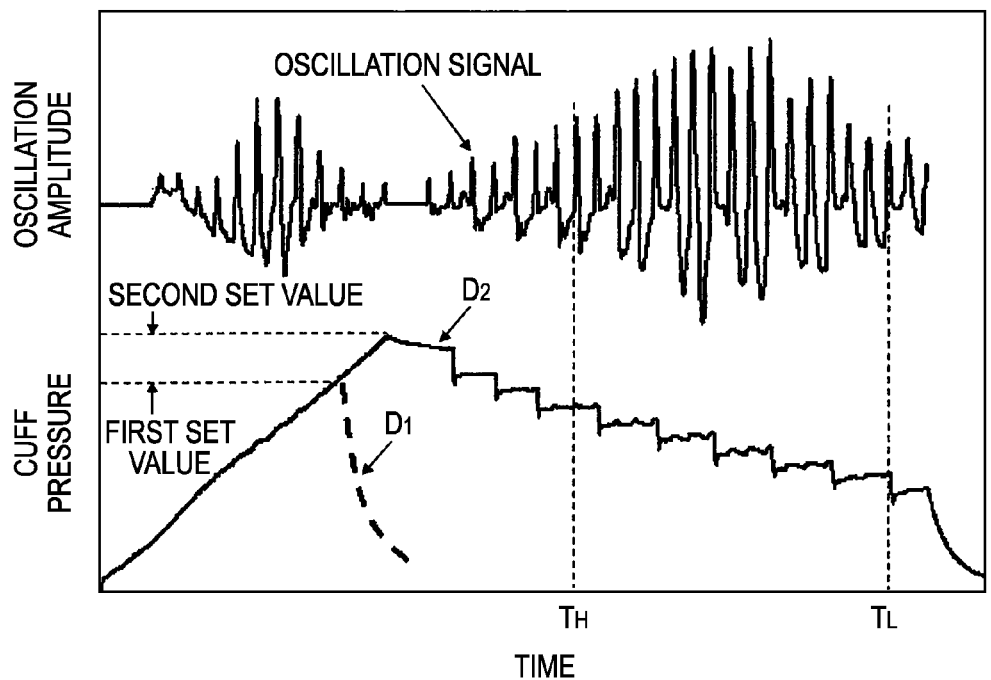
FIG. 5 is a view showing the oscillation signal and the waveform of the cuff pressure in blood pressure measurement during a process of deflating the cuff pressure in the blood pressure measuring apparatus.

By contrast, if the determination in step S8 is NO, the CPU 13b determines whether the cuff pressure is equal to or higher than the second set value or not (step S11). The operation of inflating the cuff pressure is continued until the determination in step S8 becomes YES or that in step S11 becomes YES (the cuff pressure reaches the second set value). If the determination in step S11 becomes YES, the pressure-deflating measurement such as shown in FIG. 5 is performed. FIG. 5 is a view showing the oscillation signal and the waveform of the cuff pressure in blood pressure measurement during the process of deflating the cuff pressure in the blood pressure measuring apparatus 100. In the pressure-deflating measurement, the CPU 13b transmits the control signal C2 to the electromagnetic-valve driver 12, and controls the opening of the electromagnetic valve 4 to lower the cuff pressure in a stepwise manner (step S12). As a result, as shown in FIG. 5, the cuff pressure $D_2$ due to the pressure signal D is deflated in a stepwise manner.

As shown in FIG. 5, as the cuff pressure $D_2$ is further deflated, the detected oscillation signal becomes the systolic blood pressure (maximum blood pressure) at a change point $T_H$ where the amplitude is suddenly increased, the amplitude is gradually reduced after the amplitude is increased and becomes maximum, and the detected oscillation signal becomes the diastolic blood pressure (minimum blood pressure) at a change point $T_L$ where the amplitude is suddenly reduced.

During the process of deflating the cuff pressure, the CPU 13b performs sampling on the oscillation signal to obtain the amplitude, as described above, finds a change point where the amplitude is suddenly changed, and specifies the diastolic blood pressure (minimum blood pressure) and the systolic blood pressure (maximum blood pressure) (step S13). Then, the CPU 13b determines whether both the diastolic blood pressure (minimum blood pressure) and the systolic blood pressure (maximum blood pressure) can be specified or not (step S14).

Similarly as described above, in the process of specifying the systolic and diastolic blood pressures, any related-art technique may be employed in place of the above-described technique. For example, a cuff pressure at a timing when the amplitude is at 50% of the maximum amplitude of the oscillation signal may be specified as the systolic and diastolic blood pressures.

If the determination in step S14 is YES, the CPU 13b transmits the control signal C2 to the electromagnetic-valve driver 12 to fully open the electromagnetic valve 4, thereby rapidly deflating the cuff pressure $D_2$ (step S15). Then, the CPU 13b stores the measured blood pressures in the RAM 13c or displays the blood pressures on the LCD 15, or performs the both operations (step S16), and ends the blood pressure measurement.

In the embodiment, the blood pressure measurement during the process of deflating the cuff pressure is performed while deflating the cuff pressure in a stepwise manner. Similarly as the blood pressure measurement during the process of inflating the cuff pressure, alternatively, the blood pressure measurement may be performed while deflating the cuff pressure in a linear manner. In the alternative, as compared with the case where the blood pressure measurement is performed while deflating the cuff pressure in a stepwise manner, when the subject experiences arrhythmia or body motion is caused, rapid blood pressure measurement is often enabled although the accuracy is impaired.

By contrast, if the determination in step S14 is NO, the CPU 13b determines whether the cuff pressure $D_2$ is equal to or lower than a predetermined value or not (step S17). The operation of deflating the cuff pressure in a stepwise manner is continued until the determination in step S14 becomes YES or that in step S17 becomes YES.

If the determination in step S17 is YES, the CPU 13b transmits the control signal C2 to the electromagnetic-valve driver 12 to fully open the electromagnetic valve 4, thereby rapidly deflating the cuff pressure $D_2$ (step S18). Then, contents indicating that blood pressure measurement was disabled are displaced on the LCD 5 (step S19).

As described above, according to the blood pressure measuring apparatus of the embodiment, even in the case where, during the process of inflating the cuff pressure, oscillation due to driving of the air pump is superimposed as noise on pressure oscillation in the cuff caused by pulsation, the cycle of oscillation due to the driving of the air pump is largely different from that (pulsation cycle) of the principal component of a pulse wave. Therefore, it is possible to measure a correct blood pressure from the oscillation signal which is detected when the cuff pressure is inflated. In the case where the measured blood pressure is appropriate, the inflating of the cuff pressure is ended and the cuff pressure is immediately released. Therefore, the measurement time can be shortened, and hence the burden on the subject (the patient or the like) due to the measurement is low.

Even in the case where during the process of inflating the cuff pressure a appropriate blood pressure cannot be measured because body motion, arrhythmia, or the like of the subject, the blood pressure can be then measured by pressure-deflating measurement in which the cuff pressure that is hardly affected by body motion, arrhythmia, or the like is deflated in a stepwise manner.

In the blood pressure measuring apparatus of the invention, when both the systolic and diastolic blood pressures which are measured in the process of inflating the cuff pressure are appropriate, the pressure is rapidly deflated. Therefore, it is possible to realize accurate blood pressure measurement which can be rapidly performed, and in which the burden on the subject (the patient or the like) is low.

Moreover, the cycle of air ejection by the air pump is different from that of the pulse wave, and hence ejection noise due to the operation of the air pump is superimposed as obvious noise on the oscillation signal. Therefore, the ejection noise can be distinctly removed, and hence it is possible to perform accurate blood pressure measurement.

The air pump ejects air with a short cycle (a cycle which is shorter than at least one fifth of a cycle of the principal component of the pulse wave). Therefore, the cuff can be pressurized in a substantially linear manner, and rapid blood pressure measurement is realized in the process of inflating the cuff pressure.

The flow of air ejected by the air pump can be continuously changed from a low flow (about 0.1 L/minute) to a high flow (about 3 L/minute). Therefore, the pressurization is not performed in a stepwise manner, and rapid blood pressure measurement is realized in the process of inflating the cuff pressure.

Since the pressure is inflated in a substantially linear manner, rapid blood pressure measurement is realized in the process of inflating the cuff pressure.

In the case where the blood pressure measurement in pressure inflating is inappropriate (the measurement value is not a appropriate value), the cuff is further pressurized to the second set value, and the usual blood pressure measurement performed during the process of deflating the cuff pressure can be performed. Therefore, rapid blood pressure measurement is realized. Particularly, rapid blood pressure measurement is realized in the process of inflating the cuff pressure, and accurate blood pressure measurement is realized in the process of deflating the cuff pressure, so that blood pressure measurement can be surely performed by one process of inflating and deflating the cuff pressure. Therefore, the number of occurrences of remeasuring the blood pressure can be reduced.

The pressure is deflated in a stepwise manner. Even in the case where the subject (the patient or the like) experiences arrhythmia or body motion is caused, therefore, the oscillation signal can be surely detected, with the result that rapid and accurate blood pressure measurement is realized. Alternatively, the pressure is deflated in a substantially linear manner, and hence rapid blood pressure measurement is realized in the process of deflating the cuff pressure.

The first set value in the process of inflating the cuff pressure is lower than the related-art set value (second set value). When blood pressure measurement in the process of inflating the cuff pressure is appropriate, therefore, blood pressure measurement which is rapid, and in which the burden is low is realized.

The pressure can be inflated in accordance with the size of the cuff, and the blood pressure measurement can be accurately performed in the process of inflating the cuff pressure.

What is claimed is:

1. A blood pressure measuring apparatus, configured to measure a blood pressure of a living body, the blood pressure measuring apparatus comprising:
    a cuff-pressure control unit configured to control a cuff pressure of a cuff that presses a part of the living body;
    an oscillation signal detection unit configured to detect an oscillation signal from the cuff pressure;
    a blood pressure specification unit configured to measure systolic and diastolic blood pressures as the blood pressure of the living body from the oscillation signal; and
    a blood pressure determination unit configured to determine whether the systolic and diastolic blood pressures are appropriately measured by the blood pressure specification unit based on the oscillation signal detected by the oscillation signal detection unit and previously stored criteria in the blood pressure measuring apparatus,
    wherein the cuff-pressure control unit is further configured to control the cuff pressure to be inflated to a first set value, the blood pressure specification unit is further configured to specify the systolic and diastolic blood pressures based on a change of the oscillation signal that is detected by the oscillation signal detection unit during inflation of the cuff pressure to the first set value, and when the blood pressure determination unit determines that both the systolic and diastolic blood pressures are determined to be appropriately measured by the blood pressure specification unit based on the oscillation signal detected by the oscillation signal detection unit during inflation of the cuff pressure to the first set value, the cuff-pressure control unit is configured to end the inflating of the cuff pressure of the cuff to release the cuff pressure, and
    wherein when the blood pressure determination unit determines that at least one of the systolic and diastolic blood pressures is determined not to be appropriately measured by the blood pressure specification unit based on the oscillation signal detected by the oscillation signal detection unit when the cuff pressure is inflated to the first set value, the cuff-pressure control unit controls the cuff pressure to be inflated to a second set value greater than the first set value, and then the cuff pressure to be deflated, and the blood pressure specification unit is further configured to specify the systolic and diastolic blood pressures based on the change of the oscillation signal that is detected by the oscillation signal detection unit during deflation of the cuff pressure from the second set value.

2. The blood pressure measuring apparatus according to claim 1, further comprising:
    an air pump controlled by the cuff-pressure control unit and configured to eject air to the cuff, thereby inflating the cuff pressure,
    wherein the cuff-pressure control unit is further configured to control the air pump to eject air to the cuff with a cycle which is different from a 10 cycle of a pulse wave.

3. The blood pressure measuring apparatus according to claim 2, wherein the cuff-pressure control unit is further configured to control the air pump so that the cycle at which the air pump ejects air is a cycle which is shorter than at least one fifth of the cycle of the pulse wave.

4. The blood pressure measuring apparatus according to claim 2, wherein the air pump is further configured to eject a flow of air at a rate from 0.1 20 L/minute to 3.0 L/minute.

5. The blood pressure measuring apparatus according to claim 1, wherein the cuff-pressure control unit is further configured to control the cuff pressure to be inflated in a substantially linear manner.

6. The blood pressure measuring apparatus according to claim 1, wherein the cuff-pressure control unit is further configured to control the cuff pressure to be deflated in a stepwise manner.

7. The blood pressure measuring apparatus according to claim 1, wherein the cuff-pressure control unit is further configured to control the cuff pressure to be deflated in a substantially linear manner.

8. The blood pressure measuring apparatus according to claim 1, wherein the first set value is a value which is higher than a than the systolic blood pressure of the living body, and the second set value is a value which is higher than a value in which at least 30 mmHg to 50 mmHg is added to a systolic blood pressure of the living body.

9. The blood pressure measuring apparatus according to claim 1, further comprising: a cuff-size specification unit configured to specify a size of the cuff when the cuff pressure is to be inflated, wherein the cuff-pressure control unit is further configured to control pressure inflating of the cuff based on the size of the cuff which is specified by the cuff-size specification unit.

10. The blood pressure measuring apparatus according to claim 1, wherein the cuff-pressure control unit is further configured to inflate or deflate the cuff pressure in a range of 5 mmHg/sec to 20 mmHg/sec.

11. A blood pressure measuring apparatus, configured to measure a blood pressure of a living body, the blood pressure measuring apparatus comprising:

a central processing unit (CPU) configured to control a cuff pressure of a cuff that presses a part of the living body, detect an oscillation signal from the cuff, determine whether systolic and diastolic blood pressures as the blood pressure of the living body are able to be measured from the oscillation signal, and measure the systolic and diastolic blood pressures based on the oscillation signal in response to determining that the systolic and diastolic blood pressures are able to be measured from the oscillation signal, wherein the CPU is further configured to control the cuff pressure to be inflated to a first set value, determine whether the systolic and the diastolic blood pressures as the blood pressure of the living body are able to be measured from the oscillation signal during inflation of the cuff pressure to the first set value, measure the systolic and diastolic blood pressures based on a change of the oscillation signal that is detected during the inflation of the cuff pressure to the first set value in response to determining that the systolic and diastolic blood pressures are able to be measured from the oscillation signal, and end the inflating of the cuff pressure of the cuff and release the cuff pressure, and in response to determining that the systolic and diastolic blood pressures are unable to be measured from the oscillation signal during inflation of the cuff pressure to the first set value, control the cuff pressure to be inflated to a second set value greater than the first set value, control the cuff pressure to be deflated, and measure the systolic and diastolic blood pressures based on the change of the oscillation signal that is detected during the deflation of the cuff pressure from the second set value.

* * * * *